US006753339B1

(12) United States Patent
Chazalet et al.

(10) Patent No.: US 6,753,339 B1

(45) Date of Patent: Jun. 22, 2004

(54) FUNGICIDE COMPOSITIONS

(75) Inventors: Maurice Chazalet, Anse (FR); Patrice Duvert, Lyons (FR); Jean-Marie Gouot, Saint Cyr au Mont D'Or (FR); Richard Mercer, Ecully (FR)

(73) Assignee: Aventis Cropscience SA (FR)

( * ) Notice: Subject to any disclaimer, the term of this patent is extended or adjusted under 35 U.S.C. 154(b) by 0 days.

(21) Appl. No.: 09/787,631

(22) PCT Filed: Sep. 20, 1999

(86) PCT No.: PCT/FR99/02223

§ 371 (c)(1), (2), (4) Date: Apr. 13, 2001

(87) PCT Pub. No.: WO00/16629

PCT Pub. Date: Mar. 30, 2000

(30) Foreign Application Priority Data

Sep. 21, 1998 (FR) .......................................... 98 11895

(51) Int. Cl.[7] ........................ A01N 43/78; A01N 43/50; A01N 47/10

(52) U.S. Cl. ........................ 514/367; 514/391; 514/479

(58) Field of Search ................................ 514/391, 367, 514/479

(56) References Cited

U.S. PATENT DOCUMENTS 6,384,067 B2 5/2002 Chazalet et al. ............ 514/386

FOREIGN PATENT DOCUMENTS

| | | |
|---|---|---|
| EP | 0472996 | 3/1992 |
| EP | 0472996 A1 | 3/1992 |
| EP | 0629616 A2 | 12/1994 |
| EP | 0629616 | 12/1994 |
| EP | 0775696 A1 | 5/1997 |
| EP | 0775696 | 5/1997 |
| FR | 2751845 | 2/1998 |
| WO | 9603044 | 2/1996 |
| WO | 96/03044 | 2/1996 |

OTHER PUBLICATIONS

Budavari , Merck Index, 11th ed., 1989, monograph 4964, p. 803.*

Colby, Calculating Synergistic and Antagonistic Responses of Herbicide Combinations, Weeds, pp. 20–22.

* cited by examiner

*Primary Examiner*—Sreeni Padmanabhan
*Assistant Examiner*—San-ming Hui
(74) *Attorney, Agent, or Firm*—Ostrolenk, Faber, Gerb & Soffen, LLP

(57) ABSTRACT

The invention concerns fungicide compositions comprising a compound (I) which is (4-S)-4-mehtyl-2-methylthio-4-phenyl-1-phenylamino-2-imidazoline-5-one and a compound (II) which is $N^1$-[(R)-1-(6-fluoro-2-benzothiazolyl) ethyl]-$N^2$-isopropoxycarbonyl-L-validamide or isopropyl[2-methyl-1-(phenylethyl-carbamoyl)propyl]carbamate; the compound (I)/compound (II) ratio ranges between 10 and 0.01, preferably between 5 and 0.5. The invention also concerns a method for eradicating or preventing phytopathogenic fungi in crops, characterized in that it consists in applying on the aerial parts of plants an efficient and non-phytotoxic amount of one of said fungicide compositions.

13 Claims, No Drawings

FUNGICIDE COMPOSITIONS

The present invention relates to novel fungicidal compositions comprising a 2-imidazolin-5-one derivative and an amino acid amide derivative, which are intended in particular for protecting crops. The invention also relates to a process for protecting crops against fungal diseases.

Compounds derived from 2-imidazolin-5-ones with fungicidal action are known, in particular from European patent application EP 551,048, these compounds making it possible to prevent the growth and development of phytopathogenic fungi which attack or are liable to attack crops.

International patent application WO 96/03044 also discloses a certain number of fungicidal compositions comprising a 2-imidazolin-5-one in combination with one or more fungicidal active materials.

Patent applications EP-A-0,775,696 and EP-A-0,472,966 present novel compounds for fungicidal use which have an amino acid amide structure.

However, it is always desirable to improve the products which can be used by growers in order to control fungal diseases of crops, and in particular mildews.

It is also always desirable to reduce the doses of chemical products spread into the environment to control fungal attacks on crops, in particular by reducing the application doses of the products.

Lastly, it is always desirable to increase the number of antifungal products available to growers in order for them to find, among these products, the one which is best suited to their specific use.

One aim of the invention is thus to provide a novel fungicidal composition which is useful for the problems outlined above.

Another aim of the invention is to propose a novel fungicidal composition which is useful in the preventive and curative treatment of fungal diseases, for example of Solanacea plants and of grapevine.

Another aim of the invention is to propose a novel fungicidal composition which is of improved efficacy against mildew and/or Septoria leaf blotch in Solanacea plants and grapevine.

Another aim of the invention is to propose a novel fungicidal composition which is of improved efficacy against mildew and/or oidium and/or botrytis in grapevine.

It has now been found that these aims may be achieved, partly or totally, by means of the fungicidal compositions according to the present invention.

The subject of the present invention is thus, firstly, fungicidal compositions comprising a compound (I) of formula:

(I)

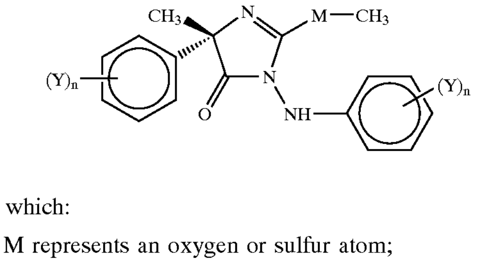

in which:

M represents an oxygen or sulfur atom;

n is an integer equal to 0 or 1;

Y is a fluorine or chlorine atom or a methyl radical;

and a compound of formula (II):

(II)

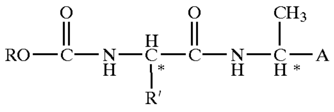

in which:

R and R', which ate identical or different, are chosen, independently of each other, from a linear or branched alkyl radical containing from 1 to 6 carbon atoms, A represents a group chosen from A1 and A2 which have the respective formulae:

(A1)

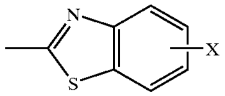

and (A2)

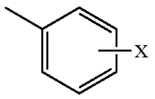

X represents the hydrogen atom, a halogen atom chosen from chlorine, fluorine, bromine and iodine, a linear or branched alkyl radical containing from 1 to 6 carbon atoms, or a linear or branched alkoxy radical containing from 1 to 6 carbon atoms, and the asterisks represent asymmetric centers;

the compound (I)/compound (II) ratio being between 50 and 0.01, preferably between 10 and 0.01 and even more preferably between 5 and 0.5.

The preferred compounds of formula (II) for the fungicidal compositions according to the invention are such that the asymmetric carbon center of the amino acid gives it the L configuration.

It is clearly understood that all the possible configurations of compound (II), i.e. all the isomers formed by the various configurations of the two asymmetric carbons, are included in the field of the present invention.

It is clearly understood that said fungicidal compositions can include a single compound (I) or more than one such compound and/or a single compound (II) or ore than one such compound, as well as another fungicidal compound, depending on the use for which they are intended.

The compositions according to the invention are advantageous for controlling, in particular, mildew and Septoria leaf blotch in crops, such as cucumber or pea, for example, in Solanacea plants, such as potato or tomato, as well as for controlling mildew in grapevine.

The compositions according to the invention can also be used for controlling other phytopathogenic diseases of crops which are well known to The person skilled in the art who has at his or her disposal the compounds of formula (I) and of formula (II).

Compound (I) is known, in particular, from patent application EP-A-0,629,616.

Compound (II), when A represents the group A1, and its use as a fungicide are described in particular in European patent application EP-A-0,775,696.

Compound (II), when A represents the group A2, and its use as a fungicide are described in particular in European patent application EP-A-0,472,996.

The compound (I)/compound (II) ratio is defined as being the ratio of the weight of these 2 compounds. This is likewise the case for any ratio of 2 chemical compounds, mentioned hereinbelow in the present text, insofar as a definition different from this ratio is not expressly indicated.

These compositions generally appreciably improve the respective and isolated action of compound (I) and of compound (II) for a certain number of fungi that are particularly harmful in crops, in particular for Solanaceae, more particularly for mildew in Solanacea plants, while at the same time retaining an absence of phytotoxicity toward these crops. This therefore results in an improvement in the spectrum of activity and a possibility of decreasing the respective dose of each active material used, the latter quality being particularly advantageous for readily appreciated ecological reasons.

The fungicidal compositions according to the invention for which:

compound (I) is the compound of formula (I) in which M is a sulfur atom and n is equal to 0, also known as (4-S)-4-methyl-2-methylthio-4-phenyl-1-phenylamino-2-imidazolin-5-one, referred to hereinbelow as "Compound A", and compound (IIA) is the compound of formula (II) in which R represents the isopropyl radical, A represents the group (A1), X represents the fluorine atom placed in position 6 on the 2-benzothiazolyl radical, the amino acid has the L configuration and the asymmetric carbon borne by the 2-benzothiazolyl radical, the R configuration, also known as $N^1$-[(R)-1-(6-fluoro-2-benzothiazolyl)ethyl]-$N^2$-isopropoxycarbonyl-L-valinamide, referred to hereinbelow as "Compound B", or alternatively compound (IIB) is the compound of formula (II) in which R represents the isopropyl radical, A represents the group (A2), X represents the methyl radical placed in position 4 on the phenyl radical, whether it is in the form of a racemate or mixtures of enantiomers and/or of diastereoisomers or in the form of a pure optical isomer, also known as isopropyl [2-methyl-1-(1-phenylethylcarbamoyl)-propyl]carbamate, referred to hereinbelow as "Compound C", are preferred.

A particularly advantageous form of compound (C) is the product commonly called Iprovalicarb.

In the compositions according to the invention, the compound (I)/compound (II) ratio is advantageously chosen so as to produce a synergistic effect. The term synergistic effect is understood to refer in particular to that defined by Colby S. R. in an article entitled "Calculation of the synergistic and antagonistic responses of herbicide combinations" published in the journal Weeds, 1967, 15, p. 20–22. The latter article uses the formula:

$$E=X+Y-XY/100$$

in which E represents the expected percentage of inhibition of the disease for the combination of the two fungicides at defined doses (for example equal to x and y respectively), X is the percentage of inhibition observed for the disease by the compound (I) at a defined dose (equal to x), Y is the percentage of inhibition observed for the disease by the compound (II) at a defined dose (equal to y). When the percentage of inhibition observed for the combination is greater than E, there is a synergistic effect.

The term "synergistic effect" also means the effect defined by application of the Tammes method, "Isoboles, a graphic representation of synergism in pesticides" Netherlands Journal of Plant Pathology, 70(1964), p. 73–80.

The compound (I)/compound (II) ratio ranges indicated above do not in any way limit the scope of the invention, but are, rather, mentioned as a guide, a person skilled in the art being entirely capable of carrying out additional tests to find other values of the ratio of doses of these two compounds, for which a synergistic effect is observed.

The compositions according to the invention, comprising compound (I) and compound (II), make it possible to observe entirely noteworthy synergistic properties.

According to one variant of the compositions according to the invention, the compound (I)/compound (II) ratio is advantageously between 10 and 0.01, preferably between 5 and 0.2.

In general, the compositions according to the invention have shown good results when the compound (I)/compound (II) ratio is between 5 and 1.

Another subject of the invention is compositions comprising one or more combinations according to the invention as described above.

The invention also comprises processes for treating plants against phytopathogenic diseases, characterized in that a combination of a compound of formula (I) and a compound of formula (II) is applied. It is also possible to apply a composition containing the two active materials, or, either simultaneously or successively so as to have the conjugated effect, two compositions each containing one of the two active materials.

These compositions cover not only compositions which are ready to be applied to the crop to be treated by means of a suitable device, such as a spraying device, but also commercial concentrated compositions which need to be diluted before they are applied onto the crop.

The present invention provides a method for controlling a large variety of phytopathogenic diseases of crops, in particular for controlling Septoria leaf blotch and mildew. These diseases can be controlled by direct application to the leaves.

The present invention thus provides a process for curatively or preventively controlling the phytopathogenic diseases of crops, which comprises treatment of said crop (for example by application or by administration) with an effective and non-phytotoxic amount of a combination as defined above. The expression "treatment of the crop" means an application or administration of a fungicidal composition as described above onto the aerial parts of the crops or onto the soil in which they are growing and which are infested or liable to become infested with a phytopathogenic disease, such as mildew or Septoria leaf blotch, for example. The expression "treatment of the crop" also means treatment of the reproduction products of the crop, such as the seeds or the tubers, for example.

The compositions described below are used in general for application onto growing vegetation, or onto areas in which crops are grown, or for the coating of or film-forming on the seeds.

Among the means which are suitable for applying the compounds of the invention, mention may be made of the use of powders, foliar sprays, granules, mists or foams, or alternatively means in the form of suspensions of finely divided or encapsulated compositions; for the treatment of soils or roots with liquid imbibitions, powders, granules, fumes or foams; for application onto the plant seeds, the use, as agents for forming a film on or coating seeds, of powders or liquid broths.

The compounds or compositions according to the invention are, appropriately, applied to the vegetation and in particular to the leaves infested with the phytopathogenic fungi. Another method for applying the compounds or compositions according to the invention is to add a formulation containing the active material, with the irrigation water. This irrigation can be an irrigation using sprinklers.

The formulations which are suitable for the applications of the compositions according to the invention comprise formulations which are suitable for use in the form, for example, of sprays, powders, granules, mists, foams, emulsions or the like.

In practice, for controlling the phytopathogenic diseases of crops, one method, for example, consists in applying an effective amount of a composition according to the invention onto the plants or onto the medium in which they are growing. For such a method, the active material is generally applied onto the same area in which the infestation needs to be controlled, at an effective dose of between about 5 g and about 2 kg of active material per hectare of area treated. Under ideal conditions, depending on the nature of the phytopathogenic fungus to be treated, a lower dose may offer adequate protection. Conversely, poor climatic conditions, resistance or other factors may require higher doses of active material. The optimum dose usually depends on several factors, for example on the type of phytopathogenic fungus to be treated, on the type or level of development of the infested plant, on the density of vegetation, or alternatively on the method of application. More preferably, an effective dose of active material is between about 20 g/ha and about 1000 g/ha.

For their use in practice, the compositions according to the invention can be used alone and can also advantageously be used in compositions containing one or other of the active materials or alternatively both of them together, in combination or association with one or more other compatible components which are, for example, solid or liquid fillers or diluents, adjuvants, surfactants or equivalents, which are suitable for the desired use and which are acceptable for uses in agriculture. The compositions can be of any type known in the sector which are suitable for application onto all types of plantations or crops. These compositions, which can be prepared in any manner known in this sector, also form part of the invention.

The compositions can also contain ingredients of other types, such as protective colloids, adhesives, thickeners, thixotropic agents, penetrating agents, oils for spraying, stabilizers, preserving agents (in particular moldproofing agents), sequestering agents or the like, as well as other known active ingredients which have pesticidal properties (in particular fungicidal, insecticidal, acaricidal or nematicidal properties) or which have properties of regulating plant growth. More generally, the compounds used in the invention can be combined with any solid or liquid additives corresponding to the usual formulation techniques.

The effective working doses of the combinations used in the invention can vary within wide proportions, in particular depending on the nature of the phytopathogenic fungi to be eliminated or the degree of infestation, for example, of the plants with these fungi.

In general, the compositions according to the invention usually contain from about 0.05% to about 99% (by weight) of one or more compositions according to the invention, from about 1% to about 95% of one or more solid or liquid fillers and, optionally, from about 0.1% to about 50% of one or more other compatible compounds, such as surfactants or the like.

In the present account, the term “filler” means an organic or inorganic, natural or synthetic component with which the active component is combined to facilitate its application, for example, onto the plants, the seeds or the soil. This filler is consequently generally inert and it must be acceptable (for example acceptable for agronomic uses, in particular for treating plants).

The filler can be solid, for example clays, natural or synthetic silicates, silica, resins, waxes, solid fertilizers (for example ammonium salts), natural soil minerals, such as kaolins, clays, talc, lime, quartz, attapulgite, montmorillonite, bentonite or diatomaceous earths, or synthetic minerals, such as silica, alumina or silicates, in particular aluminum or magnesium silicates. The solid, fillers which are suitable for granules are as follows: natural, crushed or broken rocks, such as calcite, marble, pumice, sepiolite or dolomite; synthetic granules of inorganic or organic flours; granules of organic material such as sawdust, coconut shell, corn ear or envelope, or tobacco stem; kieselguhr, tricalcium phosphate, powdered cork or adsorbent carbon black; water-soluble polymers, resins, waxes; or solid fertilizers. Such compositions can, if so desired, contain one or more compatible agents such as wetting agents, dispersing agents, emulsifiers or dyes which, when they are solid, can also act as diluents.

The fillers can also be liquid, for example: water, alcohols, in particular butanol or glycol, as well as ethers or esters thereof, in particular methyl glycol acetate; ketones, in particular acetone, cyclohexanone, methyl ethyl ketone, methyl isobutyl ketone or isophorone; petroleum fractions such as paraffinic or aromatic hydrocarbons, in particular xylenes or alkylnaphthalenes; mineral or plant oils; aliphatic chlorohydrocarbons, in particular trichloroethane or methylene chloride; aromatic chlorohydrocarbons, in particular chlorobenzenes; water-soluble or highly polar solvents such as dimethylformamide, dimethyl sulfoxide, N,N-dimethylacetamide or N-methylpyrrolidone; N-octylpyrrolidone, liquefied gases; or the like, whether they are taken separately or as a mixture.

The surfactant can be an emulsifier, a dispersing agent or a wetting agent, of ionic or nonionic type or a mixture of these surfactants. Among those surfactants which are used, for example, are polyacrylic acid salts, lignosulfonic acid salts, phenolsulfonic or naphthalenesulfonic acid salts, polycondensates of ethylene oxide with fatty alcohols or fatty acids or fatty esters or fatty amines, substituted phenols (in particular alkylphenols or arylphenols) ester-salts of sulfosuccinic acid, taurine derivatives (in particular alkyl taurates), phosphoric esters of alcohols or of polycondensates of ethylene oxide with phenols, fatty acid esters with polyols, or sulfate, sulfonate or phosphate functional derivatives of the compounds described above. The presence of at least one surfactant is generally essential when the active material and/or the inert filler are insoluble or only sparingly soluble in water and when the filler for said composition to be applied is water.

The compositions according to the invention can also contain other additives such as adhesives or dyes. Adhesives such as carboxymethylcellulose, or natural or synthetic polymers in the form of powders, granules or matrices, such as gum arabic, latex, polyvinylpyrrolidone, polyvinyl alcohol or polyvinyl acetate, natural phospholipids, such as cephalins or lecithins, or synthetic phospholipids can be used in the formulations. It is possible to use dyes such as inorganic pigments, such as, for example: iron oxides, titanium oxides, Prussian blue; organic dyestuffs, such as those of the alizarin, azo or metal phchalocyanin type; or of trace elements such as iron, manganese, boron, copper, cobalt, molybdenum or zinc salts.

The compositions containing the combinations of the invention, which are used to control the phytopathogenic fungi of crops, can also contain stabilizers, other fungicidal agents, insecticides, acaricides, nematicides, anti-helminths or anti-coccidoses, bactericides, attractant or repellent agents or pheromones for arthropods or vertebrates, deodorizers, flavorings or dyes.

These stabilizers can be chosen for the purpose of improving the strength, the persistence, the safety, the spectrum of action on the phytopathogenic fungi of crops or to make the composition capable Of accomplishing other useful functions for the areas treated.

By way of example, the compositions according to the invention may contain, in addition to a compound of formula (I) and a compound of formula (II), another active material possessing fungicidal properties.

Appropriately, the other fungicidal active material may be iprodione. Other fungicidal active materials may however be completely suitable without departing from the subject of the present invention.

Thus, when the other active material is iprodione, compositions which are completely appropriate are for example those containing compound (A), compound (B) and iprodione, or alternatively compound (A), compound (C) and iprodione.

For their use in agriculture, the combinations according to the invention are consequently in the form of compositions which are in a variety of solid or liquid forms.

The solid forms of the compositions which can be used are pulverulent powders (with an amount of active material, combination according to the invention, ranging up to 99%), wettable powders or granules (including water-dispersible granules), and in particular those obtained by extrusion, compacting, impregnation on a filler or by granulation using a powder (the amount of active material, combination according to the invention, in these wettable granules or powders, being between about 0.5% and about 99%). The homogeneous or heterogeneous solid-compositions containing a composition according to the invention, for example the granules, pellets, briquettes or capsules, can be used for treating stagnant or trickling waters over a relatively long period of time.

A similar effect can be obtained by using intermittent feeds or seepages of the water-dispersible concentrates as described later.

The liquid compositions comprise, for example, aqueous or non-aqueous solutions or suspensions (such as emulsifiable concentrates, emulsions, flowables, dispersions or solutions) or alternatively aerosols. The liquid compositions also comprise, in particular, emulsifiable concentrates, dispersions, emulsions, gels, fiowables, aerosols, wettable powders (or powders for spraying) dry flowables or dry pastes as liquid comDosition forms or as forms intended to form liquid compositions when they are applied, such as, for example, aqueous sprays (including those of low or ultra-low volume) or mists or aerosols.

The liquid compositions, for example in the form of soluble or emulsifiable concentrates, usuallv comprise from about 5 to about 95% by weight of active material, whereas the ready-to-use emulsions or solutions themselves contain from about 0.01 to 20% of active material. In addition to the solvent, the soluble or emulsifiable concentrates can contain, wnen necessary, from about 2 to about 50% of suitable additives, such as stabilizers, surfactants, penetrating agents, corrosion inhibitors, dyes or adhesives. Irrespective of their concentrations, the emulsions, which are particularly suitable for application onto plants, for example, can be obtained from these concentrates by dilution with water. These compositions are included in the field of compositions which can be used in the present invention. The emulsions can cover the forms of water-in-oil or oil-in-water type and they can be of tnick consistency or even in gel form.

All these aqueous dispersions or emulsions or mixtures for spraying can be applied, for example, to vegetation by any suitable means, firstly by spraying, at doses which are generally from about 100 to about 1200 liters of mixture to be sprayed per hectare, but can be higher or lower (for example of low or ultra-low volume), depending on the need or the application technique.

The concentrated suspensions, which can be applied by spraying, are prepared so as to be in the form of a fluid, stable product which does not sediment (in the case of fine grains), generally containing from about 10 to about 75% by weight of active material, from about 0.5 to about 30% of surfactants, from about 0.1 to about 10% of Theological agents, from about 0 to about 30% of suitable additives, such as antifoaming agents, corrosion inhibitors, stabilizers, penetrating agents, adhesives and, as filler, water or an organic liquid in which, the active material is insoluble or only sparingly soluble. Organic solids or inorganic salts can be dissolved in the filler in order to prevent any setting to a solid or to act as antifreeze for the water.

The wettable powders or soluble powders (powder for spraying) are generally prepared so as to contain from about 10 to about 100% by weight of active material, from about 0 to about 90% of solid filler, from about 0 to about 5% of a wetting agent, from about 0 to about 10% of a dispersant and, when necessary, from about 0 to about 80% of one or more stabilizers and/or other additives, such as penetrating agents, adhesives, anti-caking agents, dyes and the like. In order to obtain these wettable powders, the active material(s) is (are) intimately mixed in a suitable mixer with other additional substances which can be impregnated onto a porous support and is (are) ground in a mill or other suitable device designed for this purpose. This gives wettable powders whose wettabilily and suspension quality are very advantageous. They can be in suspension in water to give any type of concentration desired and this suspension can advantageously be used in particular for application to the leaves of plants.

The "water-dispersible granules" (WG) and the soluble granules (SG) have compositions which are substantially similar to those of the wettable powders. They can be prepared by granulation of the formulations described for the wettable powders, either according to a so-called wet-route process (by means of contact between the finely ground active material with the inert filler and a small amount of water, for example 1 to 20% by weight, or with an aqueous solution of a binder or a dispersing agent, followed by drying and screening), or according to a so-called dry-route process (grinding followed by compacting and screening) like those obtained by extrusion.

The doses and concentrations of the compositions formulated can vary depending on the method of application or the nature of the compositions or depending on their use. In general, the formulated compositions usually contain from about 0.00001% to about 100%, more particularly from about 0.0005% to about 80%, by weight of at least one combination according to the invention, or of all of the active materials (i.e. a composition of the invention as a mixture with other pesticidal substances or stabilizers). In concrete terms, the compositions used and their working doses will be chosen so as to obtain the effect(s) desired by the farmer, horticulturalist, forester, any technical staff responsible for controlling the phytopathogenic fungi of crops or any other person qualified in this field.

The following formulations described in Examples A to I illustrate formulations which can be used in controlling the phytopathogenic fungi of crops, which comprise, as active material, one or more compositions according to the invention. The two-letter codes given in brackets after the names of the types of formulation are the international codes usually used for denoting these formulations. The formulations described in Examples A to I can each be diluted to give a composition for spraying at suitable concentrations for use in fields or on grapevines. The general chemical descriptions of the components (for which all the following percentages are given on a weight basis) used in the formulations of Examples A to G and presented as examples below are as follows:

| Commercial name | Chemical description |
|---|---|
| Igepal BC/10 | Nonylphenol/ethylene oxide condensate |
| Soprophor BSU | Tristyrylphenol/ethylene oxide condensate |
| Arylan CA | 70% weight/volume solution of calcium dodecylbenzenesulfonate |
| Solvesso 150 | $C_{10}$ light aromatic solvent |
| Supragil WP | Alkyl naphthalenesulfonates |
| Darvan No2 | Sodium lignosulfonate |
| Celite PF | Synthetic filler based on magnesium silicate |
| Sopropon T36 | Sodium salts of polycarboxylic acids |
| Rhodopol 23 | Xanthan gum polysaccharide |
| Bentone 38 | Organic derivative of magnesium montmorillonite |
| Supragil MNS90 | Condensate of alkyl naphthalenesulfonates |
| Rhodorsil Antifoam 432 | Silicone emulsion |
| Aerosil | Microfine silicon dioxide |

Example A

A water-soluble concentrate (SL) is prepared with the following composition:

| | |
|---|---|
| Active Material | 7% |
| Igepal BC/10 | 10% |
| Water | 83% |

The active material is added to a solution of Igepal BC/10 dissolved in an amount of N-methylpyrrolidone with heating and stirring until dissolved. The solution thus obtained is adjusted to the final volume by addition of the remaining solvent.

Example B

An emulsifiable concentrate (EC) is prepared with the following composition:

| | | |
|---|---|---|
| Active material | 25% | (max.) |
| Soprophor BSU | 10% | |
| Arylan CA | 5% | |
| N-methylpyrrolidone | 50% | |
| Solvesso 150 | 10% | |

The first three components are dissolved in the N-methylpyrrolidone; the Solvesso 150 is then added to adjust to the final volume.

Example C

A wettable powder (WP) is prepared with the following composition:

| | |
|---|---|
| Active matererial | 40% |
| Supragil WP | 2% |
| Supragil MNS90 | 5% |
| Celite PF | 53% |

The ingredients are mixed together and ground in a hammer mill until a powder whose particle size is less than 50 microns is obtained.

Example D

A concentrated suspension formulation is prepared with the following composition:

| | |
|---|---|
| Active material | 40.00% |
| IGEPAL BC/10 | 1.00% |
| Sopropon T36 | 0.20% |
| Propylene glycol | 5.00% |
| Rhodopol 23 | 0.15% |
| Water | 53.65% |

The ingredients are intimately mixed and ground in a ball mill until an average particle size of less than 3 microns is obtained.

Example E

A water-dispersible granule (WG) is prepared with the following composition:

| | |
|---|---|
| Active materials | 80% |
| Darvan No 2 | 12% |
| Supragil MNS90 | 8% |
| Supragil WP | 2% |

The ingredients are mixed together, micronized in a fluid-energy mill and then granulated in a rotary granulator by spraving with water (up to 10%). The granules thus obtained are dried in a fluidized-bed dryer in order to remove the excess water.

Example F

A pulverulent powder (DP) is prepared with the following composition:

| | |
|---|---|
| Active material | 1 to 10% |
| Superfine talcum powder | 99 to 90% |

The ingredients are intimately mixed and then ground until a fine powder is obtained.

Example G

A wettable powder (WP) is prepared with the following composition:

| | |
|---|---|
| Active material | 50% |
| Igepal BC/10 | 5% |
| Aerosil | 5% |
| Celite PF | 40% |

The Igepal SC/10 is adsorbed onto the Aerosil which is then mixed with the other ingredients and ground in a hammer mill to give a wettable powder, which can be diluted with water down to a concentration of 0.001% to 2% by weight of active material and applied to an area infested with the phytopathogenic fungi of crops, which are to be destroyed by spraying.

The numerous formulations cited above are given by way of example and are not limited thereto. The person skilled in the art will be able to assess the use of the appropriate type of formulation for the specific problem he or she has to solve. In general, the formulations of WG type (water-dispersible granules) are particularly suitable for treatment processes using the compositions according to the present invention.

The fungicidal compositions according to the invention usually contain from 0.5 to 95% of the combination of compound (I) and compound (II).

This may be the concentrated composition, that is to say the commercial product combining compound (I) and compound (II). It may also be the dilute composition ready to be applied to the crops to be treated. In the latter case, the dilution with water may be carried out either using a commercial concentrated composition containing compound (I) and compound (II) (this mixture is referred to as the "ready-to-use" mixture or "ready mix"), or using the mixture prepared at the time of use (known as the "tank mix") of two commercial concentrated compositions each containing compound (I) and compound (II).

Lastly, the subject of the invention is a process for curatively or preventively controlling the phytopathogenic fungi of crops, characterized in that an effective and non-phytotoxic amount of a fungicidal composition according to the invention is applied onto the vegetation to be treated.

The phytopathogenic fungi of crops which may be combated by this process are, in particular, those:

- of the group of oomycetes:
  - of the genus Phytophthora such as Phytophthora infestans (mildew of Solanaceae, in particular late blight of potato or tomato),
  - of the family of Peronosporaceae, in particular *Plasmopara viticola* (downy mildew of grapevine), *Plasmopara halstedii* (sunflower mildew), Pseudoperonospora sp (in particular cucurbic mildew and downy mildew of hop), *Bremia lactucae* (mildew of lettuce), *Peronospora tabacinae* (downy mildew of tobacco) and *Peronospora parasitica* (downy mildew of cabbage), *Peronospora viciae* (downy mildew of pea) and *Peronospora destructor* (downy mildew of onion);
- of the group of adelbomycetes:
  - of the genus Alternaria, for example *Alternaria solani* (early blight of Solanaceae and in particular of tomato and potato),
  - of the genus Guignardia, in particular *Guignardia bidwelli* (black rot of grapevine),
  - of the genus Oidium, for example powdery mildew of grapevine (*Uncinula necator*), oidium of leguminous crops, for example *Erysiphe polygoni* (powdery mildew of Cruciferae), *Leveillula taurica, Erysiphe cichoracearum, Sphaerotheca fuligena* (powdery mildew of cucurbits, of composites and of tomato) *Erysiphe communis* (powdery mildew of beetroot and cabbage), *Erysiphe pisi* (powdery mildew of pea and alfalfa), *Erysiphe polyphaga* (powdery mildew of bean and cucumber mildew), *Erysiphe umbelliferarum* (powdery mildew of umbellifera, in particular of carrot), *Sphaerotheca humuli* (hop mildew);
  - of the group of soil fungi:
  - of the genus Pythium sp.,
  - of the genus Aphanomyces sp., in particular *Aphanomyces euteiches* (white root rot in pea), *Aphanomyces cochlioides* (dry rot of beet).

The expression "are applied to the vegetation to be treated" is understood to mean, for the purposes of the present text, that the fungicidal compositions which form the subject of the invention may be applied by means of various treatment processes such as:

- spraying a liquid comprising one of said compositions onto the aerial parts of said vegetation,
- dusting, incorporation of granules or powders into the soil, watering around said vegetation and, in the case of trees, injection or sprinkling,
- coating of or formation of a film on seeds of said vegetation using a broth comprising one of said compositions.

The spraying of a liquid onto the aerial parts of the crops to be treated is the preferred treatment process.

The expression "effective and non-phytotoxic amount" is understood to refer to an amount of composition according to the invention which is sufficient to allow the control or destruction of the fungi present or liable to appear on the crops, this amount entailing no symptoms of phytotoxicity for said crops. Such an amount is liable to vary within a wide range depending on the fungus to be combated, the type of crop, the climatic conditions and the nature of the compound (II) included in the fungicidal composition according to the invention. This amount may be determined by systematic field trials, which are within the capabilities of those skilled in the art.

Under the usual conditions of agricultural practice, an amount of fungicidal composition according to the invention corresponding to a dose of compound (I) of between 10 and 500 g/ha, preferably between 20 and 300 g/ha, generally gives good results.

According to the invention, the amount of fungicidal composition advantageously corresponds to a dose of compound (II) of between 10 and 500 g/ha, preferably between 20 and 300 g/ha.

The examples which follow are given purely for the purposes of illustrating the invention and do not limit it in any way.

Although the invention has been described in terms of numerous preferred variants, a person skilled in the art will appreciate that many modifications, substitutions, omissions and changes can be made without departing from the spirit of this invention. Thus, it is clearly understood that the scope of the present invention is limited only by the scope of the following claims, as well as by their equivalents.

EXAMPLE 1

Test of a Composition Against Downy Mildew of Grapevine (Preventive Action)

A composition comprising Compound A in the form of a concentrated suspension (SC) at a dose of 500 g/l and a composition comprising Compound B in the form of a wettable powder at a dose of 100 g/kg are used.

A broth containing Compound A at a dose of 125 g/l and Compound B at a dose of 37.5 g/l (Compound A/Compound B ratio approximately equal to 3.33) is prepared. This broth is diluted with water and applied as a jet sprayed onto the aerial parts of grapevine plants at a rate of 600 to 1000 l/ha depending on the degree of infestation.

This combination was studied against *Plasmopara viticola* on grapevine. The experimental procedure is described below.

Grapevine plants (var. Gamay) at the pre-blossom stage (separate floral buds) are treated with the fungicidal compositions at the doses mentioned above. An artificial contamination on the vines located around the plots is carried out by inoculation with *Plasmopara viticola* two days after the treatment.

The treatment with the broth containing Compound A and Compound B is repeated every 10 days.

Eleven days after the 7th treatment, a grading is then carried out. This consists in visually estimating the frequency (i.e. the number expressed as a percentage) of bunches or leaves which bear mildew spots (i.e. which bear a recognizable sporulating infection with a whitish down) and then, by comparison with an untreated contaminated control, in defining the practical percentage of efficacy according to the following formula:

% practical efficacy=100×(control frequency−test frequency)/control frequency

The theoretical efficacy according to the Colby formula is calculated from the following formula:

($TE$=theoretical efficacy; $PE$=practical efficacy)

$$\%TE(A+B)=\%PE(A)+\%PE(B)-(\%PE(A)\times\%PE(B)/100)$$

The theoretical efficacy according to the Colby formula is calculated from the following formula:

($TE$=theoretical efficacy; $PE$=practical efficacy)

$$\%TE(A+B)=\%PE(A)+\%PE(B)-(\%PE(A)\times\%PE(B)/100)$$

This huge difference between practical efficacy and theoretical efficacy clearly shows a large synergistic effect between the two compounds A and B.

EXAMPLE 2

Test of a Composition Against Downy Mildew of Grapevine (Curative Action)

A composition comprising Compound A in the form of a concentrated suspension (SC) at a dose of 500 g/l and a composition comprising Compound B in the form of a wettable powder at a dose of 100 g/kg are used.

A composition containing Compound A at a dose of 0.6 ppm and Compound B at a dose of 0.3 ppm (Compound A/Compound B ratio equal to 2) is prepared.

This combination was studied against *Plasmopara vicicola* on grapevine. The experimental procedure is described below.

Eight-week-old grapevine plants (var. Chardonnay) are inoculated by spraying the underside of the leaves with an aqueous suspension containing 100,000 *Plasmopara viticola* spores/ml of inoculum. The plants are then placed in a controlled-environment cabinet at 20° C., 100% RH (relative humidity) for 24 hours and are then treated with the fungicidal compositions at the doses mentioned above (3 repetitions/dose). They are then put back in the controlled-environment cabinet at 20° C., 100% RH (relative humidity) for a total of 6 days. Two gradings are then carried out (the first at 5 days and the second 1 day later). This consists in estimating the foliar area supporting a sporulating infection (recognizable by the whitish down) and, by comparison with an untreated contaminated control, in defining the percentage efficacy according to the following formula:

% practical efficacy=100×(%control contamination−% test contaminaton)/% control contaminaton The theoretical efficacy according to the Colby formula is calculated from the following formula:

($TE$=theoretical efficacy; $PE$=practical efficacy)

$$\%TE(A+B)=\%PE(A)+\%TE(B)-(\%PE(A)\times\%PE(B)/100)$$

The following results are obtained:

| | Grading | |
|---|---|---|
| | 5 days after treatment | 6 days after treatment |
| Practical efficacy (PE %) | 80 | 66.7 |
| Theoretical efficacy (TE %) | 52.8 | 39.3 |
| Synergism (PE–TE) | 27.2 | 27.4 |

Here also, strong synergism between compounds A and B is noted in this curative test on grapevine.

EXAMPLE 3

Test of a Composition Against Late Blight of Potato (Preventive Action)

The same composition as that described in the two previous examples is used (Compound A in the form of a concentrated suspension (SC) at a dose of 500 g/l and Compound B in the form of a wettable powder at a dose of 100 g/kg).

A broth containing Compound A at a dose of 100 g/l and Compound B at a dose of 25 g/l (Compound A/Compound B ratio equal to 4) is prepared. This broth is diluted with water and applied by spraying the leaves at a rate of 450 liters of broth per hectare.

This combination was studied against *Phytophthora infestans* on potato. The experimental procedure is described below.

Potato plancs (var. Up To Date) in rapid growth and before blossom are created wish the fungicidal compositions at the doses mentioned above. No artificial contamination is carried out, in order to leave the natural attack of the fungus *Phytoohthora infestans* to develop.

The treatment with the broth containing Compound A and Compound B is repeated approximately every 7 days.

Six treatments are thus carried out and the gradings are then carried out. These consist in visually estimating the percentage of destruction of all the vegetation (foliage and stalk) by the mildew and, by comparison with an untreated contaminated control, in then defining the percentage of practical efficacy as described in the previous examples.

In parallel, the theoretical efficacy according to the Colby formula is calculated.

The following results are obtained:

(In this test the untreated (control) plants are 100% destroyed)

| | Grading (days after treatment No. 6) | | |
|---|---|---|---|
| | 15 days | 23 days | 26 days |
| Practical efficacy | 76.2 | 52.5 | 40 |
| Theoretical efficacy | 47.4 | 19.1 | 16.9 |
| Synergism (PE–TE) | 28.8 | 33.4 | 23.1 |

Here also, strong synergism between compounds A and B is noted in this preventive test on potato.

EXAMPLE 4

Test of a Composition Against Late Blight of Potato (Curative Action)

The same composition as that described in the three previous examples is used (Compound A in the form of a concentrated suspension (SC) at a dose of 500 g/l and Compound B in the form of a wettable powder at a dose of 100 g/kg)

A broth containing Compound A at a dose of 150 g/l and Compound B at a dose of 37.5 g/l (Compound A/Compound B ratio equal to 4) is prepared. This broth is diluted with water and applied by spraying the leaves at a rate of 1000 liters of broth per hectare.

This combination was studied against *Phytophthora infestans* on potato. The experimental procedure is described below.

Potato plants (var. Sirtema) are taken (10 plants per plot) and their foliage is inoculated with an aqueous suspension of *Phytophthora infestans* spores (35,000 spores/ml). The leaves are then bagged to allow the growth of the fungus. After 20 hours, the bags are removed and a single treatment with the fungicidal compositions is carried out at the doses mentioned above.

Two gradings are then carried out 5 and 8 days after the treatment. These consist in visually estimating the percentage of destruction of all the vegetation (foliage and stalk) by the mildew and, by comparison with an untreated contaminated control, in then defining the percentage of practical efficacy as described in the previous examples.

In parallel, the theoretical efficacy according to the Colby formula is calculated.

The following results are obtained:

| | Grading (days after treatment) | |
|---|---|---|
| | 5 days | 8 days |
| Control | 88.4 | 90.3 |
| Practical efficacy | 66.1 | 62.3 |
| Theoretical efficacy | 44 | 42.6 |
| Synergism (PE–TE) | 22.1 | 19.7 |

This preventive test on potato once again show the synergism of the compositions according to the present invention.

What is claimed is:

1. A fungicidal composition comprising a synergistic fungicidally effective amount of:

A) compound (I), (4-S)-4-methyl-2-methylthio-4-phenyl-1-phenylamino-2-imidazolin-5-one, and B) compound (II), $N^1$-[(R)-1-(6-fluoro-2-benzothiazolyl)ethyl]-$N^2$-isopropoxycarbonyl-L-valinamide, wherein the ratio of the weight of compound (I) to the weight of compound (II) is in the range of from 5 to 0.5.

2. The fungicidal composition of claim 1 further comprising another fungicidal active material.

3. The fungicidal composition of claim 1 further comprising an agriculturally suitable inert support and optionally an agriculturally suitable surfactant.

4. The fungicidal composition of claim 1 comprising from 0.5 to 99% of the combination of compound (I) and compound (II).

5. A process for controlling the phytopathogenic fungi of crops in an area, which consists in applying a compound (I) and a compound (II) as defined in claim 1 to said area.

6. A process for controlling the phytopathogenic fungi of crops of the phytophtora and plasmopara genera comprising applying an effective and non-phytotoxic amount of the fungicidal composition of claim 1 onto the crops to be treated.

7. A process as claimed in claim 6, characterized in that the fungicidal composition is applied by spraying a liquid onto the aerial parts of the crops to be treated.

8. The process as claimed in claim 6, characterized in that the amount of fungicidal composition corresponds to a dose of compound (I) of between 10 and 500 g/ha.

9. The process as claimed in claim 6, characterized in that the amount of fungicidal composition corresponds to a dose of compound (II) of between 10 and 500 g/ha.

10. The fungicidal composition as claimed in claim 2, wherein said another fungicidal active material is iprodione.

11. The process as claimed in claim 8, wherein the amount of the fungicidal composition corresponds to a dose of compound (I) of between 20 and 300 g/ha.

12. The process as claimed in claim 9, wherein the amount of the fungicidal composition corresponds to a dose of compound (II) of between 20 and 300 g/ha.

13. A process for controlling the phytopathogenic fungi of crops of the *Phytophthora infestans* and *Plasmopara viticola* species comprising applying to said species an effective and non-phytotoxic amount of the fungicidal composition comprising:

A) compound (I), (4-S)-4-methyl-2-methylthio-4-phenyl-1-phenylamino-2-imidazolin-5-one, and B) compound (II), $N^1$-[(R)-1(6-fluoro-2-benzothiazolyl)ethyl]-$N^2$-isopropoxycarbonyl-L-valinamide.

wherein the ration of the weight of compound (I) to the weight of compound (II) is in the range of from 2 to 4 onto the crops to be treated.

* * * * *